(12) United States Patent
Causevic

(10) Patent No.: US 7,976,473 B2
(45) Date of Patent: Jul. 12, 2011

(54) METHOD AND APPARATUS FOR SIGNAL ENCODING EVOKED RESPONSES

(75) Inventor: Elvir Causevic, New York, NY (US)

(73) Assignee: Everest Biomedical Instruments Co., Chesterfield, MO (US)

( * ) Notice: Subject to any disclaimer, the term of this patent is extended or adjusted under 35 U.S.C. 154(b) by 1290 days.

(21) Appl. No.: 10/587,461

(22) PCT Filed: Jan. 28, 2005

(86) PCT No.: PCT/US2005/003401
§ 371 (c)(1),
(2), (4) Date: Jul. 25, 2006

(87) PCT Pub. No.: WO2005/072459
PCT Pub. Date: Aug. 11, 2005

(65) Prior Publication Data
US 2007/0167857 A1    Jul. 19, 2007

Related U.S. Application Data

(60) Provisional application No. 60/539,945, filed on Jan. 29, 2004.

(51) Int. Cl.
*A61B 5/00* (2006.01)
(52) U.S. Cl. ........................ 600/559; 600/558
(58) Field of Classification Search ............... 600/300, 600/301, 544, 545, 558, 559
See application file for complete search history.

(56) References Cited

U.S. PATENT DOCUMENTS

| | | | |
|---|---|---|---|
| 5,003,986 A * | 4/1991 | Finitzo et al. | 600/544 |
| 5,488,474 A | 1/1996 | Fateley et al. | |
| 2003/0125634 A1* | 7/2003 | Eda et al. | 600/544 |

OTHER PUBLICATIONS

Written Opinion of corresponding International Application No. PCT/US05/03401, Dec. 1, 2005.
Search Report of corresponding International Application No. PCT/US05/03401, Dec. 1, 2005.

* cited by examiner

*Primary Examiner* — Max Hindenburg
*Assistant Examiner* — Jonathan M Foreman
(74) *Attorney, Agent, or Firm* — Howard & Howard Attorneys PLLC

(57) ABSTRACT

A method and apparatus for utilizing the benefits of encoded signal transmission and reception to enhance the performance of medical testing devices (100) adapted to evoke and measure biological response signals such as auditory evoked potentials (AEP), and the auditory brainstem response (ABR) signals in particular. Auditory stimuli, such as clicks, are presented to the ear of a human patient, in a predetermined encoded sequence, resulting in the generation of auditory responses and bio-electric response signals in the human patient. These response signals from the patient are acquired and observed, and are processed according to the predetermined encoded sequence in which the auditory stimuli were presented to the patient's ear in order to extract the desired auditory evoked potential signals or ABR signals.

4 Claims, 4 Drawing Sheets

METHOD AND APPARATUS FOR SIGNAL ENCODING EVOKED RESPONSES

CROSS-REFERENCE TO RELATED APPLICATIONS

The present application is related to, and claims priority from, U.S. Provisional Patent Application No. 60/539,945 filed on Jan. 29, 2004, herein incorporated by reference.

TECHNICAL FIELD

The present invention is related generally to the introduction of auditory stimulus to a human ear, and to the detection of an evoked response signal and in particular, to the introduction of auditory stimulus to a human ear in a coded transmission sequence, and the detection of associated evoked response signals in a corresponding coded sequence whereby the effects of signal noise are reduced.

BACKGROUND ART

The measuring or monitoring of evoked or continuous bioelectric signals in a patient, such as an infant or other human patient who may be incapable of audiometric behavioral responses, is becoming an increasingly common method for initial patient screening or monitoring, and is used in auditory testing programs to identify hearing abnormalities, or in anesthesia and sedation monitoring to determine a patient's state, such as an awareness level.

In auditory screening, it is well known that the functionality of the outer hair cells of the inner ear can be assessed with measurements of sounds in the external ear canal generated by the inner ear, called otoacoustic emissions (OAE). The sounds which are generated by the inner ear in response to a single introduced click are called transient evoked OAE (TEOAE). Sounds in the inner ear which are generated in response to the presentation of two simultaneous tones are called distortion product OAE (DPOAE).

As shown in FIG. 1, a TEOAE is generated in response to a transient test signal, usually a sequence of discrete square waves (clicks). The level of these clicks is typically between 35 dB SPL and 90 dB SPL. In response to these test signals, a normal human ear generates a wide band response signal up to 20 ms in duration after the introduction of each click. As shown in FIG. 1, the spectrum ST of this response can be compared against the spectrum of ambient noise SA to identify normal or abnormal hearing.

Similarly, as shown in FIG. 2, a DPOAE is generated in a human ear in response to the presentation of two simultaneous tonal signals, s1 and s2 with associated frequencies f1, and f2, with f2>f2. Typically, the ratio of the frequency of f2 to f1 is selected to be about 1.2, with amplitudes |s1|=65 dB SPL and |s2|=55 db SPL in the ear canal. In response to these signals, a normal human ear generates, among others, a third tonal signal, the DPOAE at frequency $2f1-f2$, which can be measured to identify normal or abnormal hearing.

An alternative method for testing the hearing of a human patient utilizes surface electrodes to detect bioelectric signals in a human patient which are generated in response to the introduction of an auditory stimulus. These bioelectric signals can be used both in auditory screening and in brain activity monitoring during anesthesia or sedation. An auditory evoked potential (AEP) is generated in a human patient upon presentation of an auditory stimulus or series of stimuli, such as clicks or tone bursts. The AEP can be characterized by three components which refer to the latency of the bioelectric signal response with respect to the introduction of the stimulus; these are referred to as early, middle, and late AEP components.

The early or short latency component of the AEP, also known as the auditory brainstem response (ABR), occurs within the first 15 ms after the presentation of the auditory stimulus in the human ear and is widely used for clinical evaluation of hearing in infants and other individuals who are unable to effectively communicate whether a sound was detected. In individuals with normal hearing, the ABR generates a characteristic neural waveform shown in FIG. 3.

Auditory testing using the ABR typically involves a visual or statistical comparison of a tested individual's waveform to a normal template waveform. Like other evoked potentials, the ABR is recorded from surface electrodes on the scalp. However, the electrodes also record the background noise comprised of unwanted bio-potentials resulting from other neural activity, muscle activity, and unwanted non-physiological sources in the environment.

The middle component of the AEP, the auditory mid-latency response (AMLR), also referred to as the middle latency auditory evoked potential (MLAEP) occurs 15 ms-100 ms after the presentation of the auditory stimulus to the human patient, and is believed to reflect primary, non-cognitive, cortical processing of auditory stimuli. Lately, the AMLR, or MLAEP, has been of particular interest as a measure of depth of anesthesia.

It is known that the AMLR consists of positive and negative waves that are sensitive to sedatives and anesthetics. In general, increasing the level of sedation or anesthetic increases the latency of these waves, and simultaneously decreases the amplitudes. For monitoring purposes, changes in the AMLR waves are quantified as latency to peak, amplitude, and rate of change, and are sometimes combined in a single index.

Another component of the AEP, the auditory late response (ALR) occurs about 100 ms after the introduction of auditory stimulus to the human patient, and is believed to be especially sensitive to the level of sedation or anesthesia applied to a patient, and exhibits a distinct flattening of the waveform at a relatively light level of sedation or anesthesia, among other features.

It is further known that a 40 Hz auditory signal can induce an enhanced "steady-state" AEP response signal in a human patient. Conventional signal averaging over a period of time is required to extract the AEP signal from background EEG signals, and adequate responses usually may be obtainable in about 30-40 seconds. The existence of an intact AEP is believed to be a highly specific indicator for the awake state of a patient, and gradual changes in the depth of sedation or anesthesia appear to be reflected by corresponding gradual changes in the AEP.

Several methods of encoding conventional signals for transmission and reception are known which provide a resistance to signal noise. For transmitted and received signals there are two variables, frequency and time. Division by frequency, so that each pair of communicators (transmitter and receiver) is allocated part of the spectrum for all of the time, results in Frequency Division Multiple Access (FDMA). Division by time, so that each pair of communicators is allocated all (or at least a large part) of the spectrum for part of the time results in Time Division Multiple Access (TDMA). In Code Division Multiple Access (CDMA), every communicator will be allocated the entire spectrum all of the time. CDMA uses codes to identify connections. In this transmission technique, the frequency spectrum of a data-signal is spread using a code uncorrelated with that signal. As a result the bandwidth occupancy is much higher then required.

Code Division Multiple Access uses unique spreading codes to spread the baseband data before transmission. The signal is transmitted in a channel, which is below noise level. The receiver then uses a correlator to despread the wanted signal, which is passed through a narrow bandpass filter. Unwanted signals or noise will not be despread and will not pass through the filter. Spreading codes take the form of a carefully designed one/zero sequence produced at a much higher rate than that of the baseband data. The rate of a spreading code is referred to as chip rate rather than bit rate.

Accordingly, it would be advantageous to provide a method and apparatus for utilizing the benefits of a coded signal transmission and corresponding coded response reception to enhance the performance of medical testing devices adapted to introduce an auditory signal to evoke a response, and to measure bio-potentials such as auditory evoked potentials and auditory brainstem response signals.

SUMMARY OF THE INVENTION

Briefly stated, the present invention provides a method for utilizing the benefits of coded signal transmissions and corresponding coded response reception to enhance the performance of medical testing devices adapted to evoke and measure bio-potential signals such as auditory evoked potentials and auditory brainstem response signals. In a preferred embodiment, auditory stimuli, such as clicks, are presented to the ear of a human patient, in a predetermined coded sequence, resulting in the generation of corresponding coded auditory or bio-electric response signals in the human patient. These auditory or bio-electric response signals from the patient are acquired and observed, and are processed according to the predetermined coded sequence in which the auditory stimuli were presented to the patient's ear in order to extract the desired response, such as the auditory evoked potential signals or ABR signals.

In an alternate embodiment, the present invention provides a method for utilizing the benefits of coded signal transmissions and corresponding coded response reception to enhance the performance of medical testing devices adapted to evoke and measure a variety of bio-potential response signals. Stimuli selected to evoke a desired bio-potential response signal in a patient are presented to the patient in a predetermined coded sequence, resulting in the generation of corresponding coded bio-electric response signals in the patient. These bio-electric signals from the patient are acquired and observed, and are processed according to the predetermined coded sequence in which the stimuli were presented to the patient in order to extract the desired evoked potential signals for further processing.

The foregoing and other objects, features, and advantages of the invention as well as presently preferred embodiments thereof will become more apparent from the reading of the following description in connection with the accompanying drawings.

BRIEF DESCRIPTION OF THE DRAWINGS

In the accompanying drawings which form part of the specification.

Corresponding reference numerals indicate corresponding parts throughout the several figures of the drawings.

BEST MODE FOR CARRYING OUT THE INVENTION

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

The method of the present invention utilizes encoded stimuli signal transmissions to enhance the performance of a medical testing device configured to evoke and measure bio-potentials, such as auditory evoked potentials and auditory brainstem response signals. A suitable medical testing device is shown in published PCT Application No. WO 00/65983 A1 for "Handheld Audiometric Device and Method of Testing Hearing", herein incorporated by reference.

Figure 1:
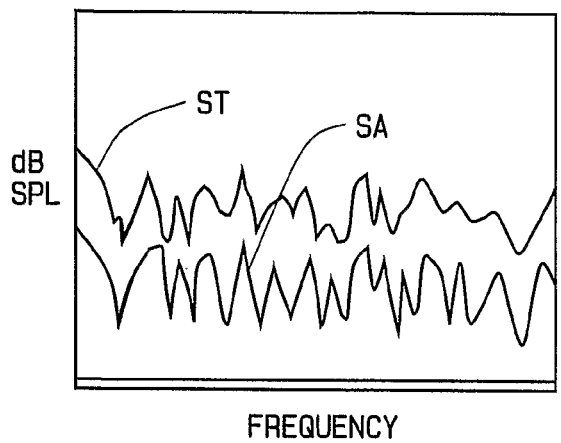
FIG. 1 is a graphical representation of a prior art TEOAE response spectrum and an ambient noise spectrum.
Figure 2:
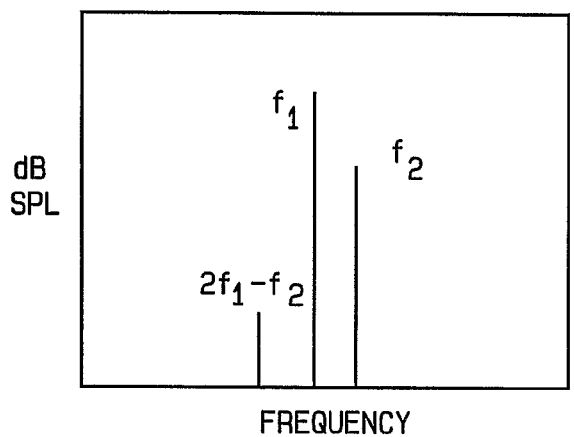
FIG. 2 is a graphical representation of a prior art pair of test tones and a typical DPOAE response tone.
Figure 3:
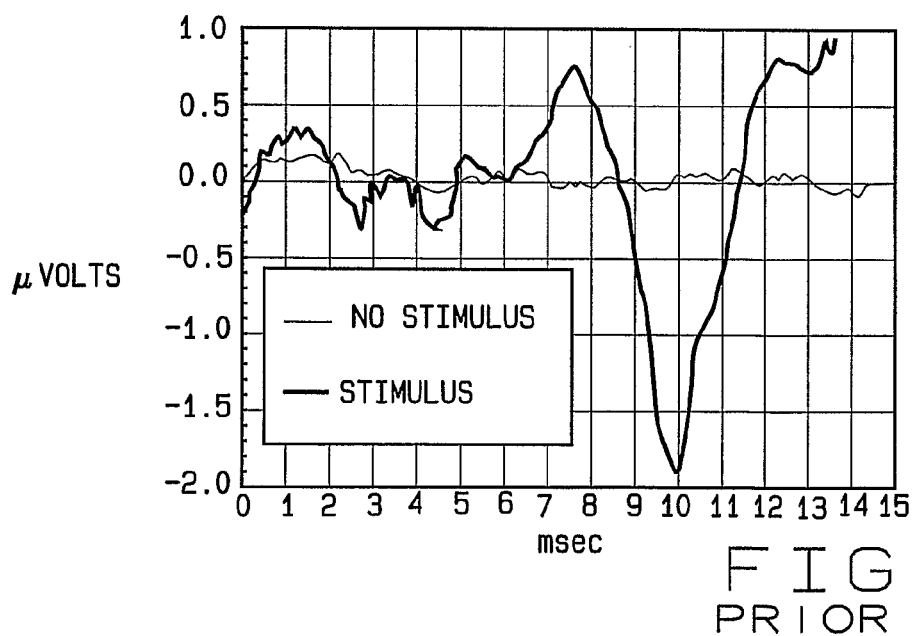
FIG. 3 is a prior art graphical representation of an auditory brainstem response to stimulus, compared with a no-stimulus signal.
Figure 4:
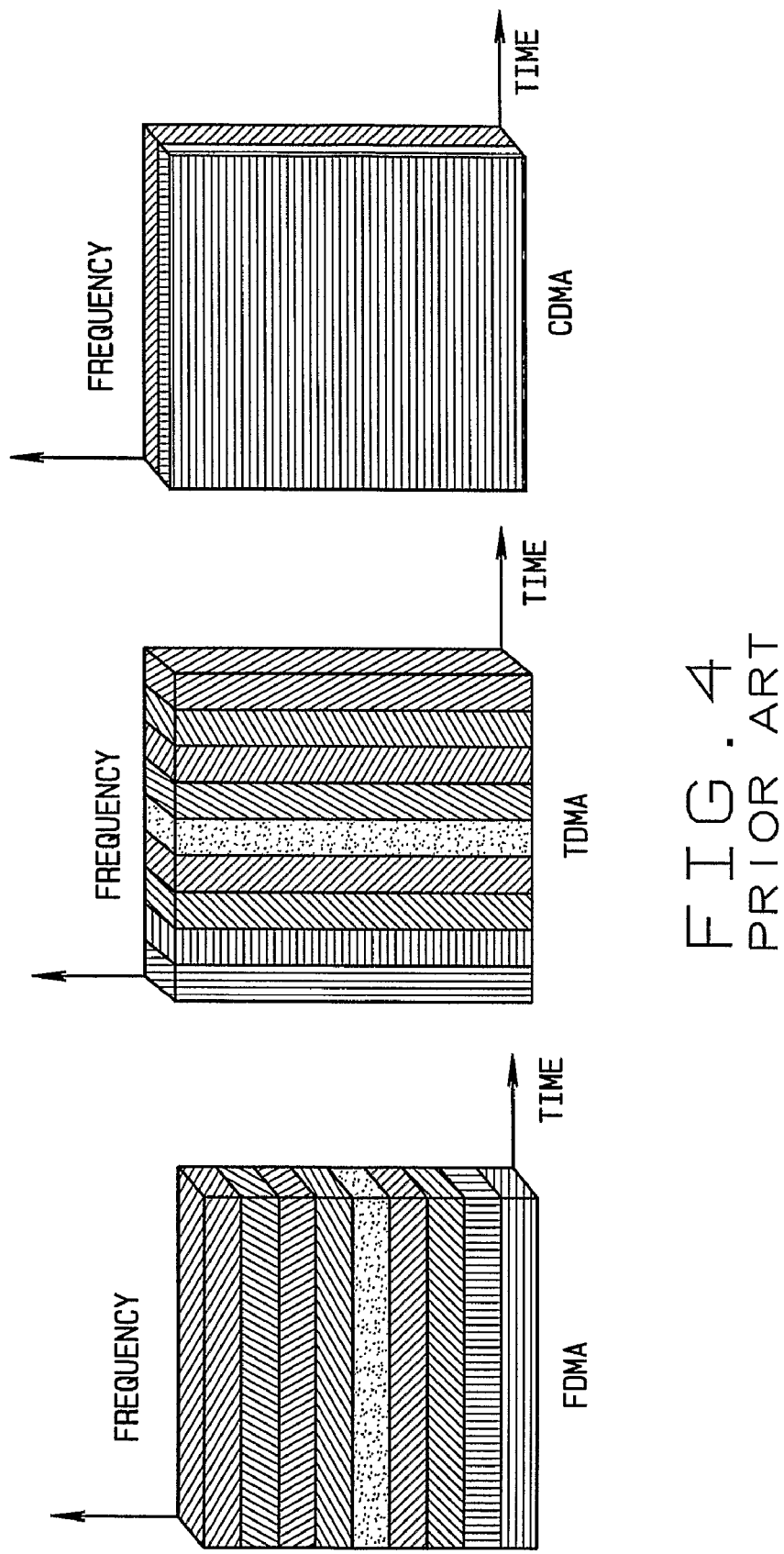
FIG. 4 is a prior art illustration of the different types of spread-spectrum signal transmission and reception techniques.
Figure 5:
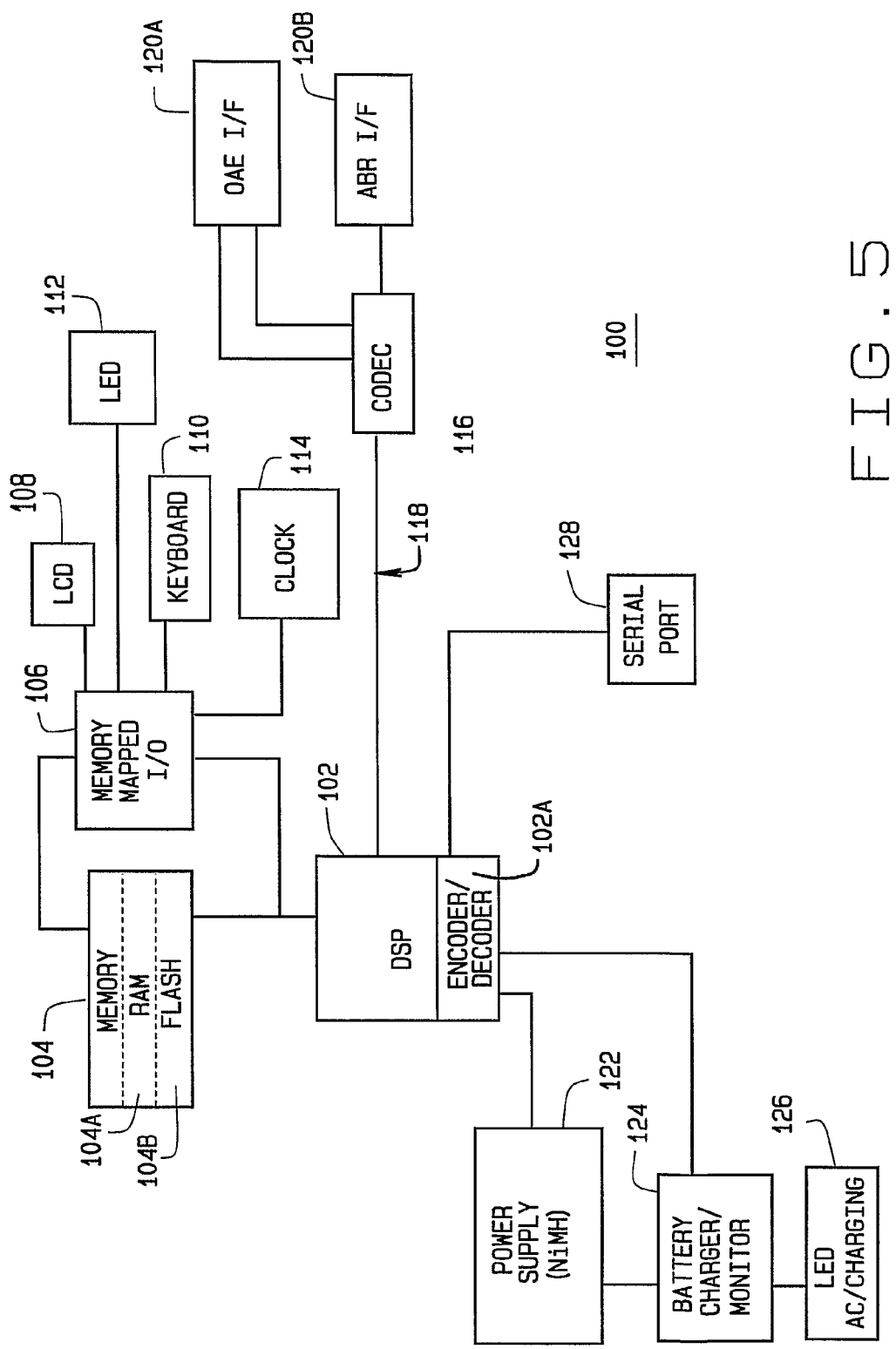
FIG. 5 is a block diagram of the components of a medical testing device of the present invention.

For example, as shown in FIG. 5, a medical testing device 100 for otoacoustic auditory emission testing and auditory brainstem response testing is configured to utilize encoded stimuli signal transmissions of the present invention. A digital signal processor 102 or other suitable logic circuit provide control for the medical testing device 100. All signal processing functions are preferably performed by the digital signal processor 102, including the execution of software instruction 102A for the encoding of stimuli signal transmissions with a spreading code prior to transmission, and the subsequent processing or decoding of received response signals.

A memory subsystem 104 is operatively connected to the digital signal processor 102. The memory subsystem 104 includes a random access memory (RAM) 104A for storing intermediate results and holding temporary variables, and a flash memory 104B for storing non-volatile, electrically programmable variables, test result data and system configuration information. A memory mapped input/output device 106 is operatively connected to the memory subsystem 104 and to the digital signal processor 102. The memory mapped input/output 106 in turn is operatively connected to an LCD display 108, a keyboard 110, an output LED indicator 112 and a real time clock 114.

The device 100 preferably enables the LCD display 108 to present signal information to a user graphically in real time on the device 100 itself, complemented with textual and numeric information about the quality of the data, signal amplitudes, signal frequency, noise floors and other related signal information.

The real-time clock 114 is operatively connected to the processor 102 through the memory mapped input/output device 106. The real-time clock 114 enables the processor 102 to provide a time stamp for each data collection or test performed.

The optional output LED 112 is used to convey test results to non-trained users to avoid confusion or misinterpretation of the LCD graphics display 108. For example, the processor 102 may be programmed to illuminate the output LED 112 when a set of predetermined input criteria, such as a signal strength are at or above a minimum value, indicative of a human patient passing an auditory screening test. The output LED 112 further allows the use of the device 100 in low light areas, where the LCD display 108 may be difficult to read or interpret.

At least one analog to digital/digital to analog coder/decoder 116 is operatively connected to the signal processor 102 along a dedicated serial link 118. As will be appreciated by those skilled in the art, the codec 116 is a special integrated circuit configured to perform analog to digital and digital to analog conversion. The codec 116 is operatively associated with one or more input/output device interfaces 120, such as an OAE interface 120A or an ABR interface 120B, which provide the functionality of the device 100 under control of the processor 102.

Other components of the medical testing device 100 which may be operatively coupled to the digital signal processor 102 include a rechargeable power supply 122 with an associated charging subsystem 124 and indicator LED 126, as well as an external data communication link, such as a serial port 128.

Those of ordinary skill in the art will recognize that the medical testing device illustrated in FIG. 5 to carry out the method of the present invention is exemplary, and that a wide variety of medical testing devices configured for the transmission of a stimulus signal to a human patient and the subsequent observation and/or measurement of a bio-response signal may be adapted to utilize the methods of the present invention, set forth below.

Figure 6:
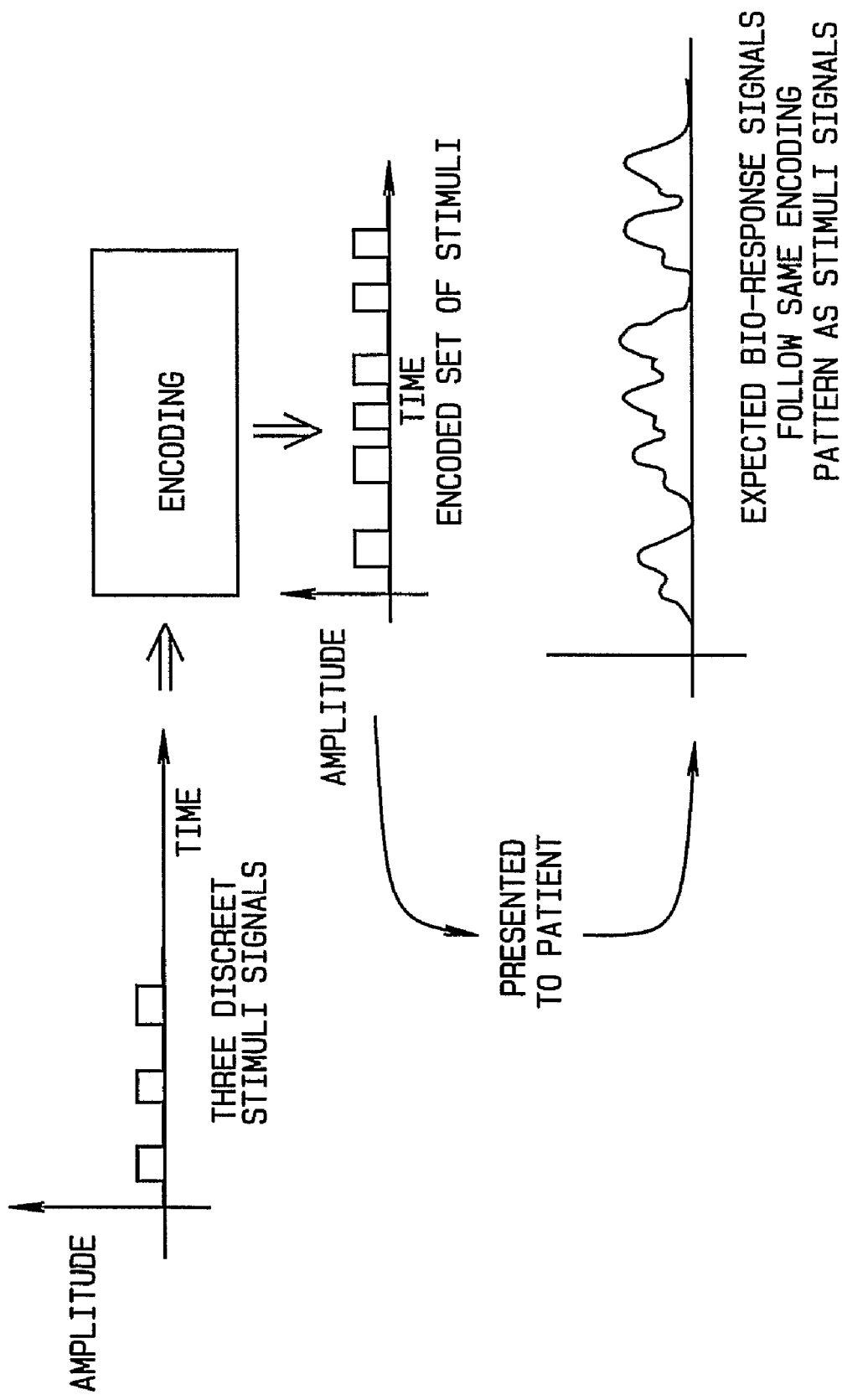
FIG. 6 is a flow-chart of a method of the present invention, illustrating a sequence of encoded stimuli delivered to a patient to producing a sequence of correspondingly encoded evoked potential responses.

Turning to FIG. 6, the basic steps in the method of the present invention are illustrated. A set of stimuli signals, such as audible clicks, tones, or flashes of light are presented by a suitable medical testing device to a human patient at a high frequency, and in a predetermined encoded sequence. For example, as shown in FIG. 6, a set of discrete and uniformly spaced stimulus signals are encoded in a predetermined pattern using a spreading code by the addition of one or more stimulus signals spaced at varying intervals. Spreading codes take the form of a predetermined one/zero sequence, and as applied to the presentation of stimuli signals, a "one" value in the sequence corresponds to the transmission of a stimulus signal, while a "zero" value in the sequence corresponds to an absence of a transmission.

The specific number and spacing of the additional stimulus signals is based on a predetermined mathematical encoding format, preferably selected from a set of transmission encoding formats which are known to be highly resistant to signal noise and interference. For example, Hadamard and Fourier encoding patterns, such as described in U.S. Pat. No. 5,488,474 to Fateley et al., herein incorporated by reference, may be utilized with suitable medical testing devices. The resulting encoded sequence of stimulus signals is then presented to the human patient in a conventional manner by the medical testing device, such as with a speaker for auditory stimuli signals, or a light for visual stimuli signals.

The stimuli signals presented to the human patient are selected to evoke known bio-potential or auditory responses, which are detectable using conventional detection devices, such as electrodes or microphones coupled to the medical testing device. These evoked response signals are contained within the background noise naturally present in electrical potential or auditory signals from the human body, and hence must be filtered and processed prior to identification. The medical testing device is configured with a correlator component, either as a dedicated circuit or as a software algorithm, to de-spread the wanted signals, which are passed through a narrow bandpass filter. Unwanted signals or noise will not be despread and will not pass through the filter. Utilizing the predetermined encoded sequence of stimulus signals as part of the filtering and processing step facilities identification of the presence and strength of the response signals by the medical testing device, allowing for accurate reconstruction of the desired response signals and filtering of undesired signal noise.

The present invention can be embodied in-part the form of computer-implemented processes and apparatuses for practicing those processes. The present invention can also be embodied in-part in the form of computer program code containing instructions embodied in tangible media, such as floppy diskettes, CD-ROMs, hard drives, or an other computer readable storage medium, wherein, when the computer program code is loaded into, and executed by, an electronic device such as a computer, micro-processor or logic circuit, the device becomes an apparatus for practicing the invention.

The present invention can also be embodied in-part in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented in a general-purpose microprocessor, the computer program code segments configure the microprocessor to create specific logic circuits.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

The invention claimed is:

1. A medical testing device for evoking and measuring response signals in a human patient, comprising:
    a processing means, said processing means configured with a software application to generate at least one predetermined sequence of stimuli signals for evoking a response in a human patient;
    a signal transmission means operatively coupled to said processing means, said signal transmission means configured to transmit said at least one sequence of stimuli signals to the human patient;
    a signal receiving means operatively coupled to said processing means, said signal receiving means configured to receive at least one unfiltered response signal from said human patient;
    wherein said processing means is further configured with a software application to process said received unfiltered response signal to extract a sequence of evoked response signals associated with said at least one predetermined sequence of stimuli signals; and
    wherein said signal transmission means is a light source.

2. The medical testing device of claim 1 wherein said predetermined sequence of stimuli signals is an encoded sequence.

3. A medical testing device for evoking and measuring response signals in a human patient, comprising:
    a processing means, said processing means configured with a software application to generate at least one predetermined sequence of stimuli signals for evoking a response in a human patient;

a signal transmission means operatively coupled to said processing means, said signal transmission means configured to transmit said at least one sequence of stimuli signals to the human patient;

a signal receiving means operatively coupled to said processing means, said signal receiving means configured to receive at least one unfiltered response signal from said human patient;

wherein said processing means is further configured with a software application to process said received unfiltered response signal to extract a sequence of evoked response signals associated with said at least one predetermined sequence of stimuli signals; and wherein said signal receiving means includes at least one microphone.

4. The medical testing device of claim 3 wherein said predetermined sequence of stimuli signals is an encoded sequence.

* * * * *